(12) United States Patent
Ji et al.

(10) Patent No.: US 10,968,488 B2
(45) Date of Patent: Apr. 6, 2021

(54) APPLICATION OF SNP (SINGLE NUCLEOTIDE POLYMORPHISM) LOCI OF WHOLE GENOME OF YAK, PRIMER GROUP FOR DETECTION AND KIT

(71) Applicants: Inst. of Animal Science and Veterinary, Tibet Academy of Agricultural and Animal Husbandry Sciences, Tibet (CN); Southwest Minzu University, Sichuan (CN); Chengdu BioInformatics Technology Ltd., Sichuan (CN)

(72) Inventors: Qiumei Ji, Tibet (CN); Jincheng Zhong, Sichuan (CN); Jinwei Xin, Tibet (CN); Zhixin Chai, Sichuan (CN); Jianhui Pang, Sichuan (CN)

(73) Assignees: Inst. of Animal Science and Veterinary, Tibet Academy of Agricultural and Animal Husbandry Sciences, Tibet (CN); Southwest Minzu University, Sichuan (CN); Chengdu BioInformatics Technology Ltd., Sichuan (CN)

( * ) Notice: Subject to any disclaimer, the term of this patent is extended or adjusted under 35 U.S.C. 154(b) by 0 days.

(21) Appl. No.: 16/321,022

(22) PCT Filed: Feb. 11, 2018

(86) PCT No.: PCT/CN2018/076240
§ 371 (c)(1),
(2) Date: Jan. 26, 2019

(87) PCT Pub. No.: WO2019/153294
PCT Pub. Date: Aug. 15, 2019

(65) Prior Publication Data
US 2019/0367996 A1 Dec. 5, 2019

(30) Foreign Application Priority Data
Feb. 7, 2018 (CN) .......................... 201810121244.3

(51) Int. Cl.
*C12Q 1/68* (2018.01)
*C12P 19/34* (2006.01)
*C12Q 1/6888* (2018.01)

(52) U.S. Cl.
CPC ..... *C12Q 1/6888* (2013.01); *C12Q 2600/124* (2013.01); *C12Q 2600/16* (2013.01)

(58) Field of Classification Search
CPC ............ C12Q 1/6888; C12Q 2600/124; C12Q 2600/156; C12Q 2600/16
See application file for complete search history.

(56) References Cited

FOREIGN PATENT DOCUMENTS

| CN | 107201409 A | 9/2017 |
| CN | 105441567 B | 10/2018 |

OTHER PUBLICATIONS

Qiu, Q., Zhang, G., Ma, T. et al. The yak genome and adaptation to life at high altitude. Nat Genet 44, 946-949. (Year: 2012).*
Hegele, R.A. "SNP Judgments and Freedom of Association" Arterioscler Thromb Vasc Biol. 2002;22:1058-1061 (Year: 2002).*
Hacker, U.T. et al. Lack of association between an interleukin-1 receptor antagonist gene polymorphisms and ulcerative colitis. Gut (1997); 40, pp. 623-627. (Year: 1997).*
Lucentini, J. "Gene Association Studies Typically Wrong", The Scientist, Dec. 20, 2004, p. 20. (Year: 2004).*
Zhixin Chai et al., "PCR-SSCP Detection and Sequence Analysis on Exon2 of ADD1 Gene in Tibetan Yak", Biotechnology Bulletin, 2012, vol. 1, pp. 124-129.
Chunnian Liang et al., "A novel single nucleotide polymorphism (SNP) of the IGF1R gene and the association with growth traits in yak", Archiv Tierzucht 53 (2010) 5, 626-628, ISSN 0003-9438.

\* cited by examiner

*Primary Examiner* — Stephen T Kapushoc
(74) *Attorney, Agent, or Firm* — Novick, Kim & Lee, PLLC; Allen Xue

(57) ABSTRACT

The 16 SNP (Single Nucleotide Polymorphism) loci of a whole genome of a yak are used in phenotypic character or molecular breeding analysis of yaks. Nucleotide sequences of the 16 SNP loci are shown in SEQ ID NO: 1-16. The 16 SNP loci can be used for providing a support for upstream and downstream processes of breeding, and the application has the advantages of high measurement accuracy, easiness in realization of standardized and automated detection, etc.

2 Claims, No Drawings
Specification includes a Sequence Listing.

ated on Feb. 19, 2019, and is 11,800 bytes in size. The information in the sequence listing is incorporated herein by reference in its entirety.

SEQUENCE LISTING

```
<160> NUMBER OF SEQ ID NOS: 48

<210> SEQ ID NO 1
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 1 agggtcctg ccccatgctc caccaggcag agcttnttct cccagcatct gagctctagg      60
cttttactca t                                                          71

<210> SEQ ID NO 2
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is t, or g

<400> SEQUENCE: 2
gggcatgata ggctaggttt ttaccctcag ggaacntaac atctaatggg agagacaatc      60
aagtaattct a                                                          71
```

```
<210> SEQ ID NO 3
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 3
ctgctggtcc cgtcaaaact ttctgcctta cagtcngccc tgctgacttg tggccgcaaa      60
gagtcaagat t                                                          71

<210> SEQ ID NO 4
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 4
cagtcggccc tgctgacttg tggccgcaaa gagtcnagat tcactcacgc gacttcacag      60
agtagacaag g                                                          71

<210> SEQ ID NO 5
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 5
gctggactaa attcagagag agagggtgg tttcantttc cagccgggac tattcattcg       60
gcaccatgca g                                                          71

<210> SEQ ID NO 6
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 6
cctgggcaag acataaaaga aaatcaagaa caaacngtta gcagtatcta aaattcttgc      60
agatcatgag g                                                          71

<210> SEQ ID NO 7
<211> LENGTH: 71
<212> TYPE: DNA
<213> ORGANISM: Artificial sequence
<220> FEATURE:
```

-continued

<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 7
tggattatct gacattgagt ctaagccaat taagancttc ctcttgtttc tcctaaagga    60
aaatacccaa g    71

<210> SEQ ID NO 8
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 8
caatgccagt accagagagc atccttcatg ccttcnttca gtaccactat tgagcaacag    60
ctgtgtgcca g    71

<210> SEQ ID NO 9
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 9
gagaaaagtc caaactatca gttaagaata acatcnatcc actaggattg tctgcactttt    60 ttaaaaaaaa t    71

<210> SEQ ID NO 10
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 10
ctccaaggct attacaacac ctttaatagt gcctcntgat tatctgatta catcacatct    60
ccaagaggtc a    71

<210> SEQ ID NO 11
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is t, or c

<400> SEQUENCE: 11
tcaaacctac tttagccaat agagtctgcc tttcangctg aactggccta ccctctgctc    60
gcatgaatgt g                                                         71

<210> SEQ ID NO 12
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is t, or g

<400> SEQUENCE: 12
cggaagaagt gccccgtaaa agtgactcag ctctcntgag ggcctgactg tctctttgaa    60
cctacccgtg t                                                         71

<210> SEQ ID NO 13
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 13
gataactagt caggtttctt tctttgtagc actttntaag ttgagcaggg tcttagcata    60
cttttgtttt g                                                         71

<210> SEQ ID NO 14
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is t, or c

<400> SEQUENCE: 14
ggcccaccac ggcctttgtg ctttgcttag gacttnagga gagagggtct ctccccaaag    60
tccagcacag g                                                         71

<210> SEQ ID NO 15
<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is a, or g

<400> SEQUENCE: 15
agaaagcact ttacatctct ttatggactg agaaangaaa ataccggctg gttgggaaag    60
gatagacaga c                                                         71

<210> SEQ ID NO 16

<211> LENGTH: 71
<212> TYPE: DNA
<213> ORGANISM: Artificial sequence
<220> FEATURE:
<223> OTHER INFORMATION: synthesized
<220> FEATURE:
<221> NAME/KEY: misc_feature
<222> LOCATION: (36)..(36)
<223> OTHER INFORMATION: n is t, or c

<400> SEQUENCE: 16
cttgcaattg attccaaagg tccttccacc tatacnctcc tcccgcccag ggcaattatt    60
cacatggcta a    71

<210> SEQ ID NO 17
<211> LENGTH: 19
<212> TYPE: DNA
<213> ORGANISM: Artificial sequence
<220> FEATURE:
<223> OTHER INFORMATION: synthesized

<400> SEQUENCE: 17
gggtcctgcc ccatgctcc    19

<210> SEQ ID NO 18
<211> LENGTH: 21
<212> TYPE: DNA
<213> ORGANISM: Artificial sequence
<220> FEATURE:
<223> OTHER INFORMATION: synthesized

<400> SEQUENCE: 18
gcctagagct cagatgctgg g    21

<210> SEQ ID NO 19
<211> LENGTH: 22
<212> TYPE: DNA
<213> ORGANISM: Artificial sequence
<220> FEATURE:
<223> OTHER INFORMATION: synthesized

<400> SEQUENCE: 19
gggcatgata ggctaggttt tt    22

<210> SEQ ID NO 20
<211> LENGTH: 25
<212> TYPE: DNA
<213> ORGANISM: Artificial sequence
<220> FEATURE:
<223> OTHER INFORMATION: synthesized

<400> SEQUENCE: 20
tagaattact tgattgtctc tccca    25

<210> SEQ ID NO 21
<211> LENGTH: 21
<212> TYPE: DNA
<213> ORGANISM: Artificial sequence
<220> FEATURE:
<223> OTHER INFORMATION: synthesized

<400> SEQUENCE: 21
ctgctggtcc cgtcaaaact t    21

<210> SEQ ID NO 22
<211> LENGTH: 21

```
<212> TYPE: DNA
<213> ORGANISM: Artificial sequence
<220> FEATURE:
<223> OTHER INFORMATION: synthesized

<400> SEQUENCE: 22
tgactctttg cggccacaag t                                              21

<210> SEQ ID NO 23
<211> LENGTH: 21
<212> TYPE: DNA
<213> ORGANISM: Artificial sequence
<220> FEATURE:
<223> OTHER INFORMATION: synthesized

<400> SEQUENCE: 23
gacttgtggc cgcaaagagt c                                              21

<210> SEQ ID NO 24
<211> LENGTH: 21
<212> TYPE: DNA
<213> ORGANISM: Artificial sequence
<220> FEATURE:
<223> OTHER INFORMATION: synthesized

<400> SEQUENCE: 24
ctgtgaagtc gcgtgagtga a                                              21

<210> SEQ ID NO 25
<211> LENGTH: 24
<212> TYPE: DNA
<213> ORGANISM: Artificial sequence
<220> FEATURE:
<223> OTHER INFORMATION: synthesized

<400> SEQUENCE: 25
gctggactaa attcagagag agag                                           24

<210> SEQ ID NO 26
<211> LENGTH: 21
<212> TYPE: DNA
<213> ORGANISM: Artificial sequence
<220> FEATURE:
<223> OTHER INFORMATION: synthesized

<400> SEQUENCE: 26
tggtgccgaa tgaatagtcc c                                              21

<210> SEQ ID NO 27
<211> LENGTH: 21
<212> TYPE: DNA
<213> ORGANISM: Artificial sequence
<220> FEATURE:
<223> OTHER INFORMATION: synthesized

<400> SEQUENCE: 27
ggcaagacat aaaagaaaat c                                              21

<210> SEQ ID NO 28
<211> LENGTH: 21
<212> TYPE: DNA
<213> ORGANISM: Artificial sequence
<220> FEATURE:
<223> OTHER INFORMATION: synthesized

<400> SEQUENCE: 28
```

-continued

```
gatactgcta accgtttgtt c                                              21

<210> SEQ ID NO 29
<211> LENGTH: 21
<212> TYPE: DNA
<213> ORGANISM: Artificial sequence
<220> FEATURE:
<223> OTHER INFORMATION: synthesized

<400> SEQUENCE: 29
tggattatct gacattgagt c                                              21

<210> SEQ ID NO 30
<211> LENGTH: 21
<212> TYPE: DNA
<213> ORGANISM: Artificial sequence
<220> FEATURE:
<223> OTHER INFORMATION: synthesized

<400> SEQUENCE: 30
ttaggagaaa caagaggaag t                                              21

<210> SEQ ID NO 31
<211> LENGTH: 21
<212> TYPE: DNA
<213> ORGANISM: Artificial sequence
<220> FEATURE:
<223> OTHER INFORMATION: synthesized

<400> SEQUENCE: 31
tgccagtacc agagagcatc c                                              21

<210> SEQ ID NO 32
<211> LENGTH: 22
<212> TYPE: DNA
<213> ORGANISM: Artificial sequence
<220> FEATURE:
<223> OTHER INFORMATION: synthesized

<400> SEQUENCE: 32
gcacacagct gttgctcaat ag                                             22

<210> SEQ ID NO 33
<211> LENGTH: 20
<212> TYPE: DNA
<213> ORGANISM: Artificial sequence
<220> FEATURE:
<223> OTHER INFORMATION: synthesized

<400> SEQUENCE: 33
gagaaaagtc caaactatca                                                20

<210> SEQ ID NO 34
<211> LENGTH: 20
<212> TYPE: DNA
<213> ORGANISM: Artificial sequence
<220> FEATURE:
<223> OTHER INFORMATION: synthesized

<400> SEQUENCE: 34
aaaagtgcag acaatcctag                                                20

<210> SEQ ID NO 35
<211> LENGTH: 20
<212> TYPE: DNA
<213> ORGANISM: Artificial sequence
```

```
<220> FEATURE:
<223> OTHER INFORMATION: synthesized

<400> SEQUENCE: 35
caacaccttt aatagtgcct                                             20

<210> SEQ ID NO 36
<211> LENGTH: 20
<212> TYPE: DNA
<213> ORGANISM: Artificial sequence
<220> FEATURE:
<223> OTHER INFORMATION: synthesized

<400> SEQUENCE: 36
acctcttgga gatgtgatgt                                             20

<210> SEQ ID NO 37
<211> LENGTH: 20
<212> TYPE: DNA
<213> ORGANISM: Artificial sequence
<220> FEATURE:
<223> OTHER INFORMATION: synthesized

<400> SEQUENCE: 37
tcaaacctac tttagccaat                                             20

<210> SEQ ID NO 38
<211> LENGTH: 20
<212> TYPE: DNA
<213> ORGANISM: Artificial sequence
<220> FEATURE:
<223> OTHER INFORMATION: synthesized

<400> SEQUENCE: 38
ttcatgcgag cagagggtag                                             20

<210> SEQ ID NO 39
<211> LENGTH: 20
<212> TYPE: DNA
<213> ORGANISM: Artificial sequence
<220> FEATURE:
<223> OTHER INFORMATION: synthesized

<400> SEQUENCE: 39
gaagaagtgc cccgtaaaag                                             20

<210> SEQ ID NO 40
<211> LENGTH: 20
<212> TYPE: DNA
<213> ORGANISM: Artificial sequence
<220> FEATURE:
<223> OTHER INFORMATION: synthesized

<400> SEQUENCE: 40
acacgggtag gttcaaagag                                             20

<210> SEQ ID NO 41
<211> LENGTH: 20
<212> TYPE: DNA
<213> ORGANISM: Artificial sequence
<220> FEATURE:
<223> OTHER INFORMATION: synthesized

<400> SEQUENCE: 41
tagtcaggtt tctttctttg                                             20
```

```
<210> SEQ ID NO 42
<211> LENGTH: 20
<212> TYPE: DNA
<213> ORGANISM: Artificial sequence
<220> FEATURE:
<223> OTHER INFORMATION: synthesized

<400> SEQUENCE: 42
caaaacaaaa gtatgctaag                                              20

<210> SEQ ID NO 43
<211> LENGTH: 20
<212> TYPE: DNA
<213> ORGANISM: Artificial sequence
<220> FEATURE:
<223> OTHER INFORMATION: synthesized

<400> SEQUENCE: 43
acggcctttg tgctttgctt                                              20

<210> SEQ ID NO 44
<211> LENGTH: 20
<212> TYPE: DNA
<213> ORGANISM: Artificial sequence
<220> FEATURE:
<223> OTHER INFORMATION: synthesized

<400> SEQUENCE: 44
tgtgctggac tttggggaga                                              20

<210> SEQ ID NO 45
<211> LENGTH: 25
<212> TYPE: DNA
<213> ORGANISM: Artificial sequence
<220> FEATURE:
<223> OTHER INFORMATION: synthesized

<400> SEQUENCE: 45
agcactttac atctctttat ggact                                        25

<210> SEQ ID NO 46
<211> LENGTH: 23
<212> TYPE: DNA
<213> ORGANISM: Artificial sequence
<220> FEATURE:
<223> OTHER INFORMATION: synthesized

<400> SEQUENCE: 46
gtctatcctt tcccaaccag ccg                                          23

<210> SEQ ID NO 47
<211> LENGTH: 20
<212> TYPE: DNA
<213> ORGANISM: Artificial sequence
<220> FEATURE:
<223> OTHER INFORMATION: synthesized

<400> SEQUENCE: 47
attgattcca aaggtccttc                                              20

<210> SEQ ID NO 48
<211> LENGTH: 20
<212> TYPE: DNA
<213> ORGANISM: Artificial sequence
<220> FEATURE:
<223> OTHER INFORMATION: synthesized
```

```
<400> SEQUENCE: 48
tagccatgtg aataattgcc                                                    20
```

APPLICATION OF SNP (SINGLE NUCLEOTIDE POLYMORPHISM) LOCI OF WHOLE GENOME OF YAK, PRIMER GROUP FOR DETECTION AND KIT

INCORPORATION OF SEQUENCE LISTING

This application contains a sequence listing submitted in Computer Readable Form (CRF). The CFR file containing the sequence listing entitled "PA119-0033-SequenceListing.txt", which was created on Feb. 19, 2019, and is 11,800 bytes in size. The information in the sequence listing is incorporated herein by reference in its entirety.

TECHNICAL FIELD

The present invention belongs to the technical field of animal husbandry and particularly relates to an application of SNP (Single Nucleotide Polymorphism) loci of a whole genome of a yak, a primer group for detection and a kit.

BACKGROUND

Yaks are special cattle, which are distributed in Qinghai-Tibet Plateau as a center and adjacent alpine and subalpine regions thereof, can make full use of pasture resources of alpine-cold grassland and have extremely high adaptability to ecological environmental conditions of the alpine-cold grassland. The yaks live freely in severe environmental conditions of thin air, short pasture growing period, cold and long grass withering period, produce offspring, provide producing and living necessities such as milk, meat, hairs, servitude and fuel for local herdsmen, are indispensable in local animal husbandry economy and can be addressed as versatile domestic animals. The yaks are an extremely precious gene pool in genetic resources. However, Chinese yaks are multiple in quantity and variety group and wide in distribution, and all yak varieties are different in phenotypes such as meat production, milk production and body type characters. And, the incompleteness of genome mutation information of Chinese local yak varieties is one of substantial reasons causing the limitation to breeding and related researches of yak varieties in our country.

Single nucleotide polymorphism (SNP) mainly means DNA sequence polymorphism caused by the mutation of a single nucleotide in a genome level. The mutation is one of the commonest biological inheritable mutations. The SNP is a publicly-known third-generation genetic marker, and many phenotype differences, disease susceptivity and so on are possibly related to the SNP. Seen from experiment operation, the discovery of phenotype related gene mutations through the SNP is easier than that through genealogy; and some SNP does not directly cause related characters, but can become an important marker as the SNP is adjacent to some related genes. At present, reports on SNP marker loci related to body weight of the yaks are absent.

Therefore, a problem to be urgently solved by those skilled in the art is to provide SNP locus information related to phenotypes of the yaks, and the SNP locus is applied to the phenotypic character or molecular breeding analysis of the yaks.

SUMMARY

An object of the present invention is to provide an application of 16 SNP (Single Nucleotide Polymorphism) loci of a whole genome of a yak in phenotypic character or molecular breeding analysis of yaks to solve the problem in the prior art that SNP loci are not applied to the phenotypic character or molecular breeding analysis of the yaks yet.

Another object of the present invention is to provide a primer group for detecting the 16 SNP loci.

Another object of the present invention is to provide a kit comprising the primer group.

Another object of the present invention is to provide a method for the phenotypic character or molecular breeding analysis of the yaks.

In order to achieve the above-mentioned objects, the present invention adopts a technical scheme as follows:

According to the application of the 16 SNP loci of the whole genome of the yak in the phenotypic character or molecular breeding analysis of the yaks, provided by the present invention, the 16 SNP loci are as follows:

AX-174702570, a nucleotide sequence is shown in SEQ ID NO: 1;
AX-174961896, a nucleotide sequence is shown in SEQ ID NO: 2;
AX-174407967, a nucleotide sequence is shown in SEQ ID NO: 3;
AX-174402854, a nucleotide sequence is shown in SEQ ID NO: 4;
AX-174929694, a nucleotide sequence is shown in SEQ ID NO: 5;
AX-174547362, a nucleotide sequence is shown in SEQ ID NO: 6;
AX-174734142, a nucleotide sequence is shown in SEQ ID NO: 7;
AX-174706158, a nucleotide sequence is shown in SEQ ID NO: 8;
AX-174783962, a nucleotide sequence is shown in SEQ ID NO: 9;
AX-174627015, a nucleotide sequence is shown in SEQ ID NO: 10;
AX-174928167, a nucleotide sequence is shown in SEQ ID NO: 11;
AX-174555047, a nucleotide sequence is shown in SEQ ID NO: 12;
AX-174845027, a nucleotide sequence is shown in SEQ ID NO: 13;
AX-174891371, a nucleotide sequence is shown in SEQ ID NO: 14;
AX-174570649, a nucleotide sequence is shown in SEQ ID NO: 15; and
AX-174620133, a nucleotide sequence is shown in SEQ ID NO: 16.

The primer group for detecting the 16 SNP loci, provided by the present invention, comprises upstream primers and downstream primers, and nucleotide sequences of the upstream primers and downstream primers are shown in SEQ ID NO:17-48.

A kit comprising the above-mentioned primer group.

The method for the phenotypic character or molecular breeding analysis of the yaks, provided by the present invention, comprises the following steps:
(1) synthesizing probe sequences corresponding to the above-mentioned 16 SNP loci; and
(2) extracting DNA from the yaks, performing PCR (Polymerase Chain Reaction) amplification by adopting the above-mentioned primer group, and judging and detecting whether the yaks are in line with the breeding requirements on heavy body weight or not from amplification bands.

Compared with the prior art, the present invention has the beneficial effects that:

The 16 SNP loci provided by the present invention come from special genetic mutation information of 32 Chinese local yak varieties, can be applied to the aspects of character related analysis, molecular assisted breeding and so on and can be used for providing a support for upstream and downstream processes of breeding. The application has the advantages of high measurement accuracy, easiness in realization of standardized and automated detection, etc.

DETAILED DESCRIPTION

The present invention is further described with reference to embodiments below, and modes of the present invention comprise, but not limited to, the following embodiments.

Thinking of the present invention is as follows: firstly, 96 yaks in all of 32 different yak varieties on a national scale are subjected to whole-genome data resequencing. The 32 yak varieties cover all yak varieties within the boundaries of our country. High-reliability loci are picked from SNP mutations of the 96 yaks and are used for producing chips. Then, 16 SNP loci related to meat production are picked by enlarging samples, using 268 yaks and using the prepared chips.

Embodiment 1

The embodiment provides a method for picking loci with maximum SNP mutation reliability from resequenced data of 96 yaks. Chips are prepared.

Firstly, 32 different local yak groups (each group comprises 3 yaks, 96 yaks in all) on a national scale are subjected to whole-genome data resequencing (the coverage of 10× for each individual) by using a sequencing platform Illumina X Ten to obtain sequenced data of 2592G. Based on this, quality control is carried out firstly to filter off data with relatively low sequencing quality. Then, all summary reads are compared to a reference genome by using comparison software BWA to generate a comparison result file in a sam format, then, the result file in the sam format is converted into a bam format for sequencing by using samtools, and finally, SNP mutations of the 96 yaks are identified by using the most universal GATK for SNP identification. Finally, some high-reliability loci are picked from the SNP mutations of the 96 yaks and are used for producing chips.

Through comparison with the existing databases of the yaks, loci mostly related to genetic characters of the yaks are identified, verified and screened, and finally, high-density yak SNP gene subtype chips containing 630209 SNP loci are designed and customized by Afymetrix.

SNP mutation screening of the resequenced data of the 96 yaks and chip preparing comprise specific steps as follows:
1. DNA Extraction.
2. DNA Sample Detection.

Detection on DNA samples mainly comprises 3 methods: (1) DNA degradation degree and whether pollution to RNA, protein and so on is present or not are analyzed by agarose gel electrophoresis. (2) the purity (OD 260/280 ratio) of DNA is detected by a Nanodrop method. (3) the concentration of DNA is accurately quantified by a Qubit method. According to the above-mentioned detection results, the DNA samples with the OD value of 1.8 to 2.0 and the content of 1.5 micrograms or more are adopted to construct a pool. The above-mentioned agarose gel electrophoresis, Nanodrop method and Qubit method are all existing technologies.

3. Data Analysis

After original sequenced reads are obtained, an information analysis process is performed referring to a genome (BosGru_v2.0) and approximately comprises the following two parts:

1) sequenced data quality evaluation: mainly counting indexes such as data volume, basic group mass, comparison ratio, coverage, capture rate and uniformity, evaluating whether pool constructing sequencing reaches standards or not, and performing subsequent analysis if the pool constructing sequencing reaches the standards.

2) mutation detection: comparing high-quality sequences to the reference genome of the yaks, detecting mutation information in the samples, and subjecting detected mutations to counting and annotation.

4. Chip Preparation

SNP information picked through resequencing is supplied to the Affymetrix, and 630209 SNP loci are finally selected through locus screening standards of an Affymetrix platform and are used for chip design and production.

Embodiment 2

The embodiment provides a method for screening meat production related character SNP loci from 268 yaks.

3 national-authenticated yak groups, including Jiali yaks, Pali yaks and Sibu yaks, (268 individuals in all) are selected, and SNP loci are screened through chips prepared in the embodiment 1. Yak individuals of 4 to 9 years old and a young and mature stage are strictly screened from each group, healthy individuals with relatively light body weight and relatively heavy body weight are screened from each group and are grouped as samples for chip screening. Body weight data of each individual are recorded in detail, GWAS analysis is performed according to obtained chip screened data, and finally, 16 loci mostly-related to meat production of the yaks are found.

Specific steps are as follows:

The gDNA of the samples is quantified by using Nano-Drop ND-2000 (Thermo Scientific) and is subjected to DNA completeness detection through gel electrophoresis. After DNA quality detection is qualified, the amplification, segmentation, precipitation and re-suspending of the samples and the crossing and wash-staining of the chips refer to chip standard flows. The gDNA is re-suspended and then is added into crossing MIX, and then, quality detection is performed. After quality detection is qualified, chip crossing, wash-staining and scanning are performed by using GeneTitan MC Instrument.

Data Analysis Part

Original data obtained through scanning by a GeneTitan system are imported into software Axiom Analysis Suite and are subjected to clustering and gene subtyping by using the software. Finally, PLINK-formatted data are exported through the software Axiom Analysis Suite and are applied to subsequent data analysis.

Information on the screened 16 SNP loci is shown in a table as follows:

| SNP Locus | Nucleotide sequence of SNP locus | Physical Position | Mutation 1 | | | Mutation 2 | | | Mutation 3 | | |
|---|---|---|---|---|---|---|---|---|---|---|---|
| | | | Mutation Type | Mutation Frequency | Body weight Correlativity | Mutation Type | Mutation Frequency | Body weight Correlativity | Mutation Type | Mutation Frequency | Body weight Correlativity |
| AX-174702570 | SEQ ID NO: 1 | 326970 | AA | 5 | + | AG | 52 | + | GG | 211 | − |
| AX-174961896 | SEQ ID NO: 2 | 327739 | TT | 211 | − | GG | 5 | + | GT | 52 | + |
| AX-174407967 | SEQ ID NO: 3 | 337514 | AA | 5 | + | AG | 52 | + | GG | 211 | − |
| AX-174402854 | SEQ ID NO: 4 | 337544 | GA | 52 | + | AA | 211 | − | GG | 5 | + |
| AX-174627015 | SEQ ID NO: 5 | 23932 | AA | 16 | + | AG | 113 | + | GG | 138 | − |
| AX-174928167 | SEQ ID NO: 6 | 82966 | TC | 89 | + | CC | 171 | − | TT | 6 | + |
| AX-174891371 | SEQ ID NO: 7 | 1168770 | TC | 8 | + | CC | 260 | − | / | / | / |
| AX-174570649 | SEQ ID NO: 8 | 1170706 | GA | 8 | + | AA | 258 | − | / | / | / |
| AX-174555047 | SEQ ID NO: 9 | 68096 | TT | 8 | + | TG | 70 | + | GG | 189 | − |
| AX-174620133 | SEQ ID NO: 10 | 2788947 | CC | 10 | − | TT | 190 | + | CT | 68 | − |
| AX-174845027 | SEQ ID NO: 11 | 491659 | AA | 10 | − | AG | 98 | − | GG | 160 | + |
| AX-174929694 | SEQ ID NO: 12 | 549280 | GA | 142 | + | AA | 83 | − | GG | 42 | + |
| AX-174783962 | SEQ ID NO: 13 | 223744 | AA | 27 | + | AG | 140 | + | GG | 99 | − |
| AX-174547362 | SEQ ID NO: 14 | 539922 | AA | 26 | + | AG | 141 | + | GG | 101 | − |
| AX-174734142 | SEQ ID NO: 15 | 561203 | AA | 4 | − | AG | 68 | − | GG | 196 | + |
| AX-174706158 | SEQ ID NO: 16 | 123435 | GA | 68 | − | AA | 196 | + | GG | 4 | − |

Relationship between each genotype of each locus and body weight, "+" represents positive correlation, and "−" represents negative correlation

Embodiment 3

The embodiment provides a primer group for detecting the 16 SNP loci screened in the embodiment 1, and corresponding relationships between nucleotide sequences of the primer group and the SNP loci are shown in a table as follows:

| SNP locus | Nucleotide sequence of SNP locus | Sense primer (5'-3') nucleotide sequence | Antisense primer (5'-3') nucleotide sequence |
| --- | --- | --- | --- |
| AX-174702570 | SEQ ID NO: 1 | SEQ ID NO: 17 | SEQ ID NO: 18 |
| AX-174961896 | SEQ ID NO: 2 | SEQ ID NO: 19 | SEQ ID NO: 20 |
| AX-174407967 | SEQ ID NO: 3 | SEQ ID NO: 21 | SEQ ID NO: 22 |
| AX-174402854 | SEQ ID NO: 4 | SEQ ID NO: 23 | SEQ ID NO: 24 |
| AX-174929694 | SEQ ID NO: 5 | SEQ ID NO: 25 | SEQ ID NO: 26 |
| AX-174547362 | SEQ ID NO: 6 | SEQ ID NO: 27 | SEQ ID NO: 28 |
| AX-174734142 | SEQ ID NO: 7 | SEQ ID NO: 29 | SEQ ID NO: 30 |
| AX-174706158 | SEQ ID NO: 8 | SEQ ID NO: 31 | SEQ ID NO: 32 |
| AX-174783962 | SEQ ID NO: 9 | SEQ ID NO: 33 | SEQ ID NO: 34 |
| AX-174627015 | SEQ ID NO: 10 | SEQ ID NO: 35 | SEQ ID NO: 36 |
| AX-174928167 | SEQ ID NO: 11 | SEQ ID NO: 37 | SEQ ID NO: 38 |
| AX-174555047 | SEQ ID NO: 12 | SEQ ID NO: 39 | SEQ ID NO: 40 |
| AX-174845027 | SEQ ID NO: 13 | SEQ ID NO: 41 | SEQ ID NO: 42 |
| AX-174891371 | SEQ ID NO: 14 | SEQ ID NO: 43 | SEQ ID NO: 44 |
| AX-174570649 | SEQ ID NO: 15 | SEQ ID NO: 45 | SEQ ID NO: 46 |
| AX-174620133 | SEQ ID NO: 16 | SEQ ID NO: 47 | SEQ ID NO: 48 |

Embodiment 4

The embodiment provides an application method of the 16 SNP loci in phenotypic character and molecular assisted breeding of yaks, comprising the specific steps:

Synthesizing probe sequences corresponding to the 16 loci, collecting yak ear samples, extracting DNA, carrying out quality control, and then, performing PCR amplification by adopting the primer group provided by the present invention, and judging and detecting whether the yaks are in line with the breeding requirements on heavy body weight or not from amplification bands. In which, the synthesis of the probe sequences, the extraction of yak DNA and the PCR amplification are all the existing technologies. If band mutation loci amplified according to primers are marked with "+", it is proven that corresponding individuals are relatively heavy in body weight; and if band mutation loci amplified according to primers are marked with "−", it is proven that corresponding individuals are relatively light in body weight. Therefore, molecular detection can be performed on the 16 loci of bulls and cows, if both the bulls and the cows carry high-body-weight analysis marker loci, the bulls and the cows can mate preferably, descendants of the bulls and the cows are selectively bred, through reproduction of several generations, the body weight of the yaks can be greatly increased, the meat producing capability is improved, and real income is brought for people of grazing areas.

The above-mentioned embodiments are only preferred embodiments of the present invention and should not be used for limiting the scope of protection of the present invention; and all changes or modifications without substantive meaning, which are made on the basis of main body design thinking and spirit of the present invention and solve technical problems consistent with those solved by the present invention, shall fall within the scope of protection of the present invention.

The invention claimed is:

1. A method of screening a yak to determine its genotype, comprising:

obtaining a sample of genetic material from said yak; and
assaying each of the following 16 SNP (Single Nucleotide Polymorphism) loci in the sample to detect genetic markers in said yak:
AX-174702570, at position 36 of the nucleotide sequence as shown in SEQ ID NO: 1;
AX-174961896, at position 36 of the nucleotide sequence as shown in SEQ ID NO: 2;
AX-174407967, at position 36 of the nucleotide sequence as shown in SEQ ID NO: 3;
AX-174402854, at position 36 of the nucleotide sequence as shown in SEQ ID NO: 4;
AX-174929694, at position 36 of the nucleotide sequence as shown in SEQ ID NO: 5;
AX-174547362, at position 36 of the nucleotide sequence as shown in SEQ ID NO: 6;
AX-174734142, at position 36 of the nucleotide sequence as shown in SEQ ID NO: 7;
AX-174706158, at position 36 of the nucleotide sequence as shown in SEQ ID NO: 8;
AX-174783962, at position 36 of the nucleotide sequence as shown in SEQ ID NO: 9;
AX-174627015, at position 36 of the nucleotide sequence as shown in SEQ ID NO: 10;
AX-174928167, at position 36 of the nucleotide sequence as shown in SEQ ID NO: 11;
AX-174555047, at position 36 of the nucleotide sequence as shown in SEQ ID NO: 12;
AX-174845027, at position 36 of the nucleotide sequence as shown in SEQ ID NO: 13;
AX-174891371, at position 36 of the nucleotide sequence as shown in SEQ ID NO: 14;
AX-174570649, at position 36 of the nucleotide sequence as shown in SEQ ID NO: 15; and
AX-174620133, at position 36 of the nucleotide sequence as shown in SEQ ID NO: 16.

2. A method according to claim 1, further comprising the following steps:

performing PCR (Polymerase Chain Reaction) amplification by adopting the primer group comprising upstream primers and downstream primers shown in SEQ ID NO: 17-48, and detecting the presence of at least one genotype, the genotype selected from the group consisting of:
AA or AG at SNP locus AX-174702570,
GG or GT at SNP locus AX-174961896,
AA or AG at SNP locus AX-174407967,
GA or GG at SNP locus AX-174402854,
TC or TT at SNP locus AX-174547362,
GG at SNP locus AX-174734142,
TT at SNP locus AX-174706158,
AA or AG at SNP locus AX-174783962,
AA or AG at SNP locus AX-174627015,
AA or AG at SNP locus AX-174928167,
CC at SNP locus AX-174845027,
AG at SNP locus AX-174891371,
GA at SNP locus AX-174570649, and
AA at SNP locus AX-174620133,
wherein the presence of the at least one genotype indicates the yak is associated with a trait of increased body weight.

\* \* \* \* \*